United States Patent [19]
Reed et al.

[11] Patent Number: 5,227,856
[45] Date of Patent: Jul. 13, 1993

[54] SAMPLE HOLDING AND POSITIONING MECHANISM AND METHOD FOR OPTICAL ANALYSIS

[75] Inventors: David S. Reed, Truckee, Calif.; Robert C. Funk, Auburn, Ill.

[73] Assignee: Perten Instruments North America Inc., Reno, Nev.

[21] Appl. No.: 848,692

[22] Filed: Mar. 9, 1992

[51] Int. Cl.⁵ .............................. G01N 21/03
[52] U.S. Cl. ..................... 356/244; 356/446
[58] Field of Search ........................ 356/244, 446

[56] References Cited

U.S. PATENT DOCUMENTS

| | | | |
|---|---|---|---|
| 4,040,747 | 9/1977 | Webster | 356/446 |
| 4,692,620 | 9/1987 | Rosenthal | 250/341 |
| 4,695,727 | 9/1987 | Brierley et al. | 250/328 |
| 4,752,689 | 6/1988 | Satake | 356/446 |

*Primary Examiner*—Richard A. Rosenberger
*Attorney, Agent, or Firm*—Flehr Hohbach Test Albritton & Herbert

[57] ABSTRACT

A sample holding apparatus (20) and method for use with an optical analyzing assembly (10) for irradiating a sample (33) with light energy. The sample holder apparatus (20) comprises a sample container (30) having a downwardly facing container opening (44), and a partition (32) movably positioned over the opening (44). A container support (24) is positioned adjacent the partition (32) and includes a surface (26) having an analyzing window (28) for transmitting the light energy therethrough. The container (30) is movably mounted to a transport mechanism (36) which permits the partition (32) to slidably retract from a closed position, across the opening (44), to an open position as the container (30) is urged onto the support surface (26). Consequently, the sample (33) contained in the container (30) is exposed and drawn into direct contact with the analyzing window (28). The wall members (38) of the container (30) retain the particulates of the sample (33) in substantially a same position during the relative movement.

22 Claims, 5 Drawing Sheets

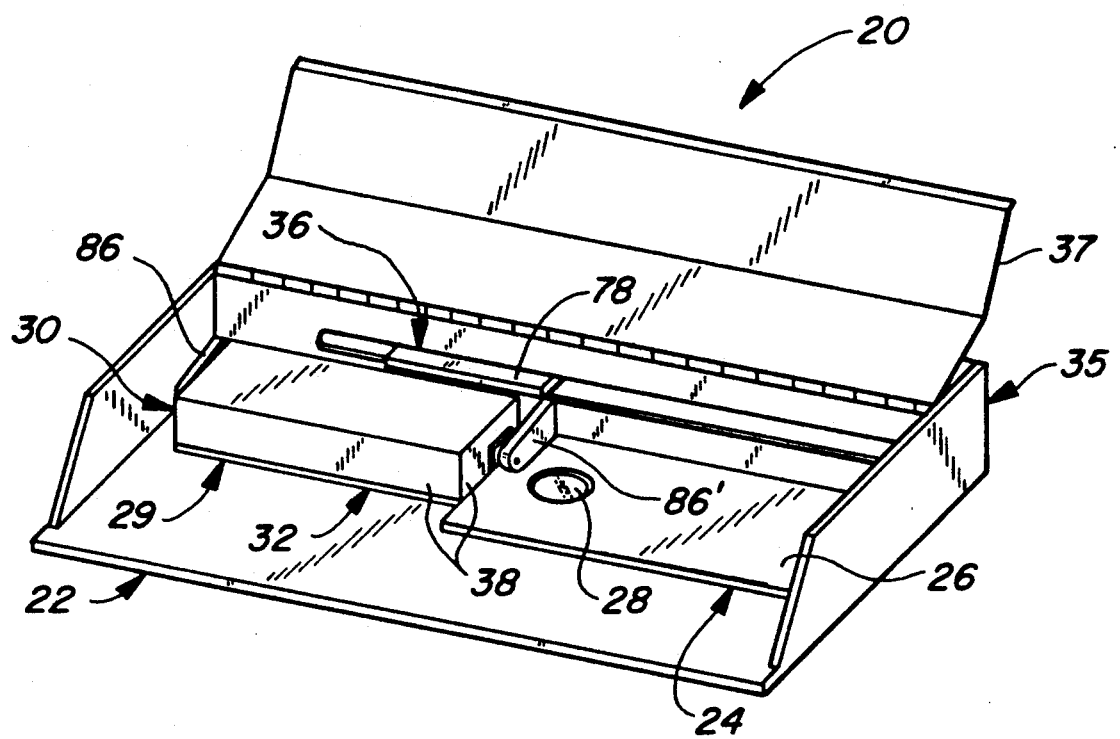
FIG._1
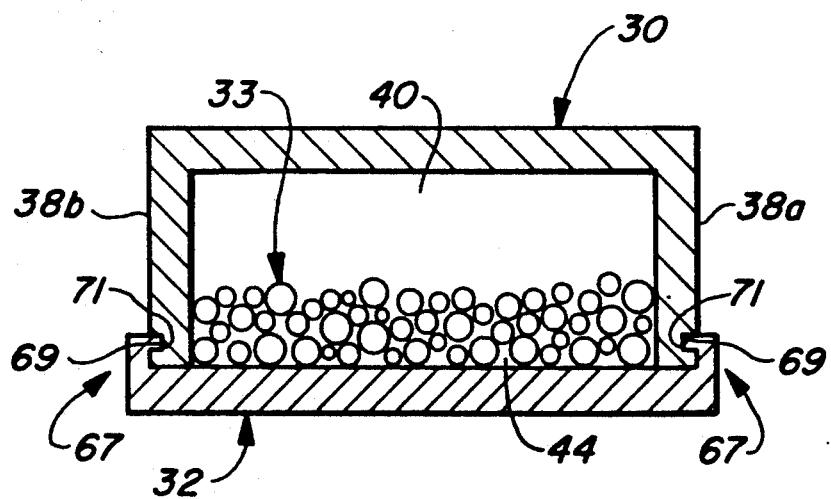
FIG._7

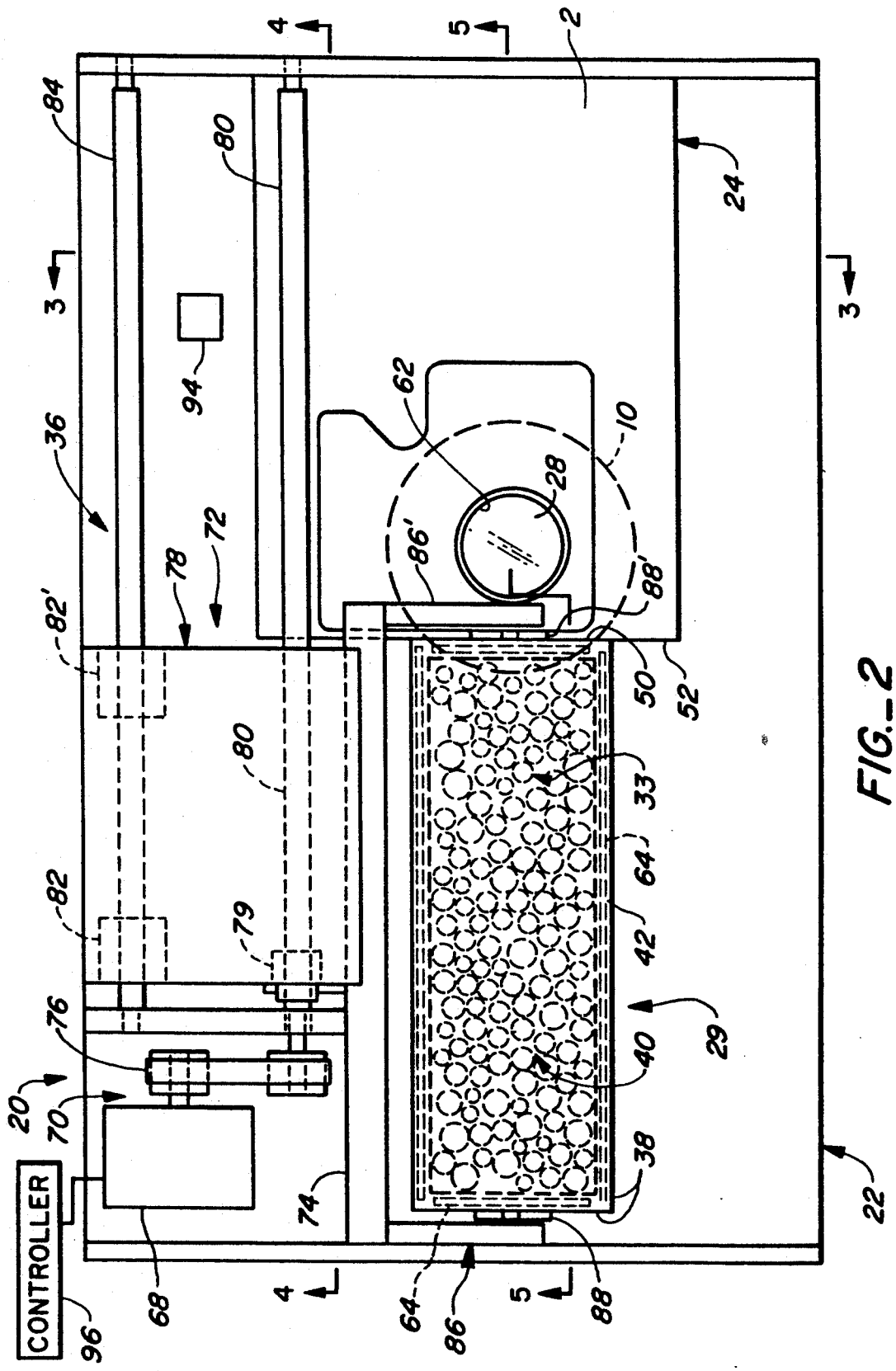
FIG._2

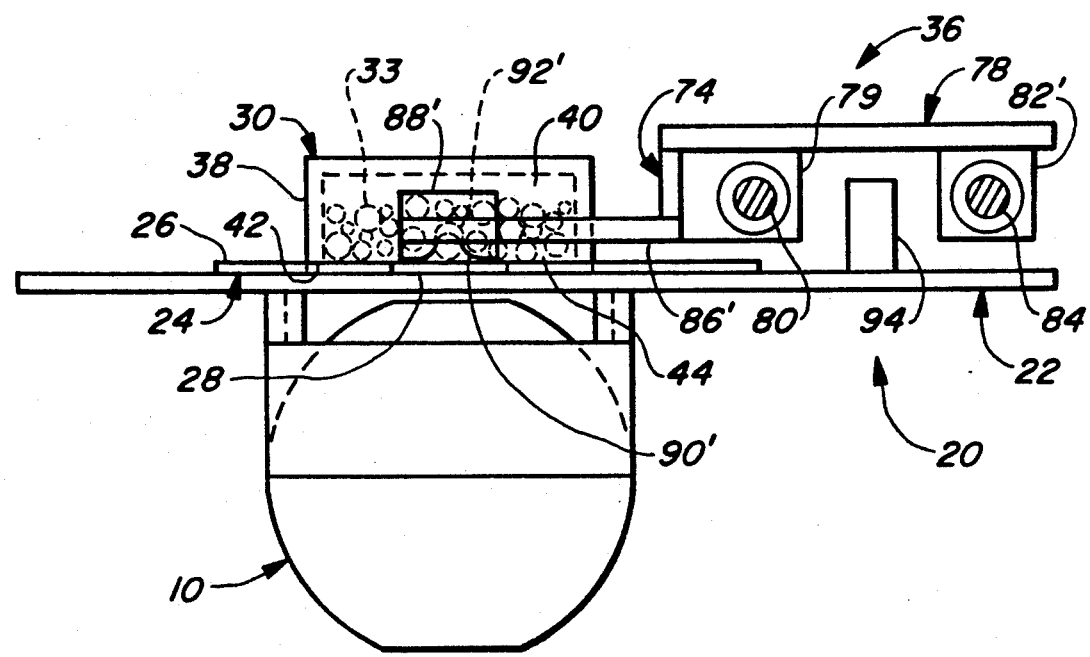
FIG._3
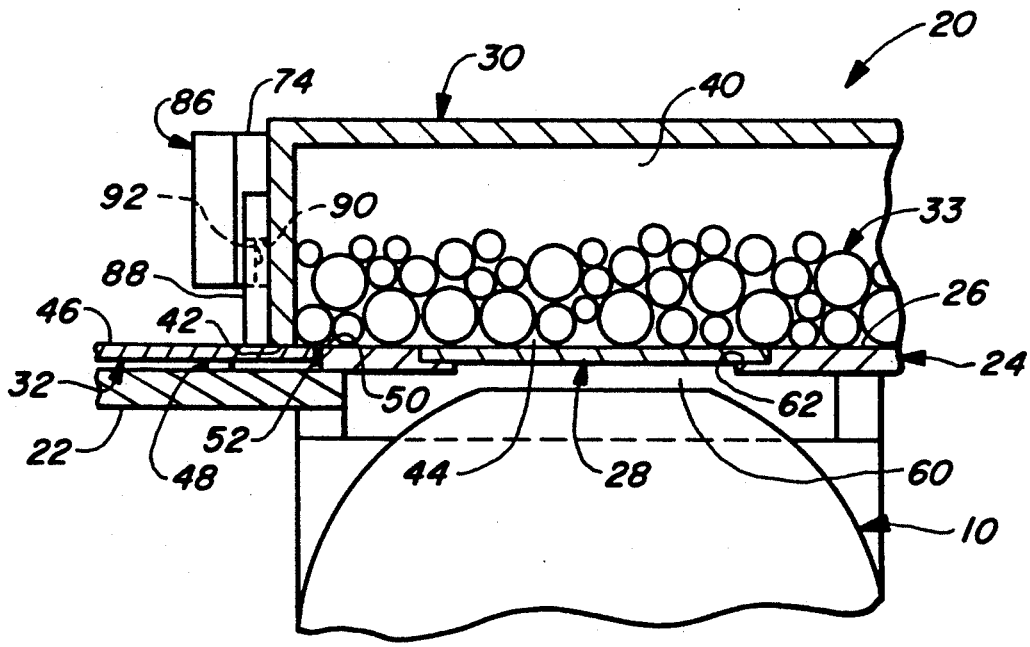
FIG._6

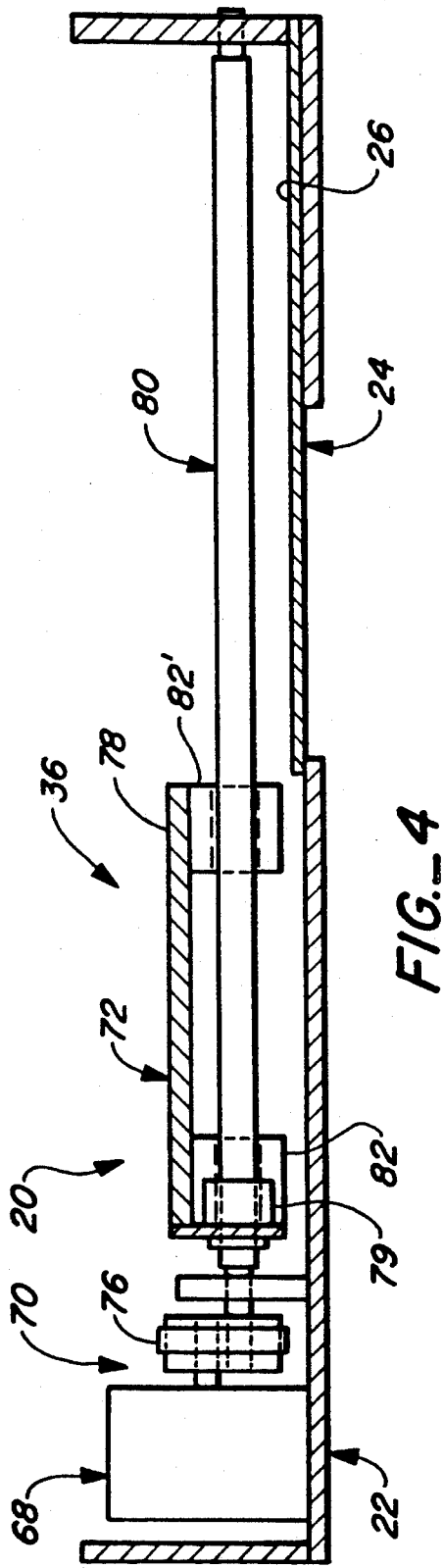
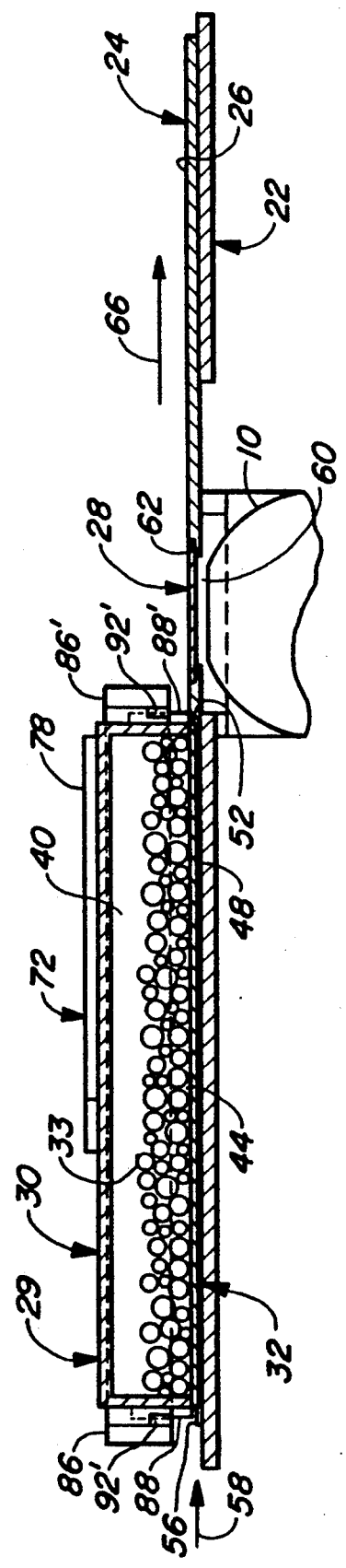

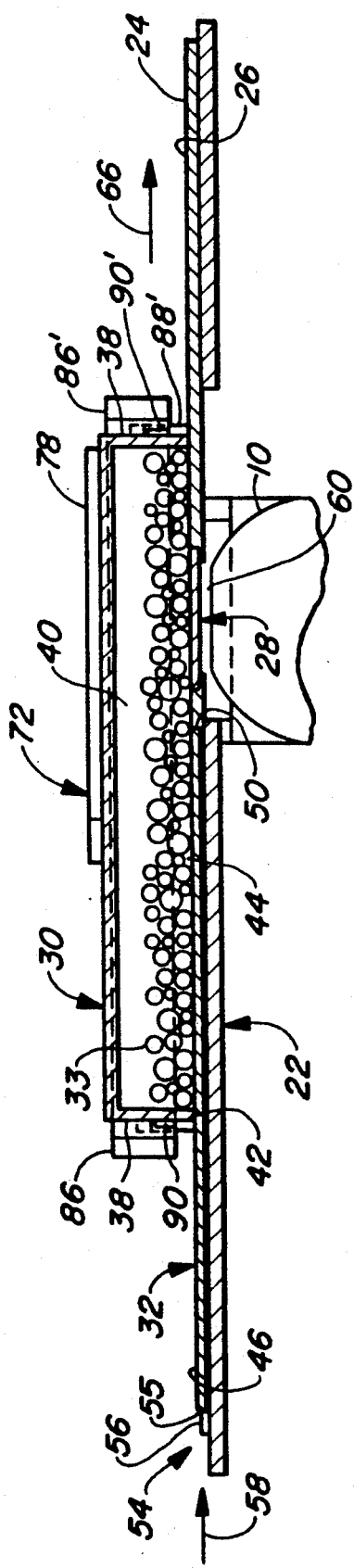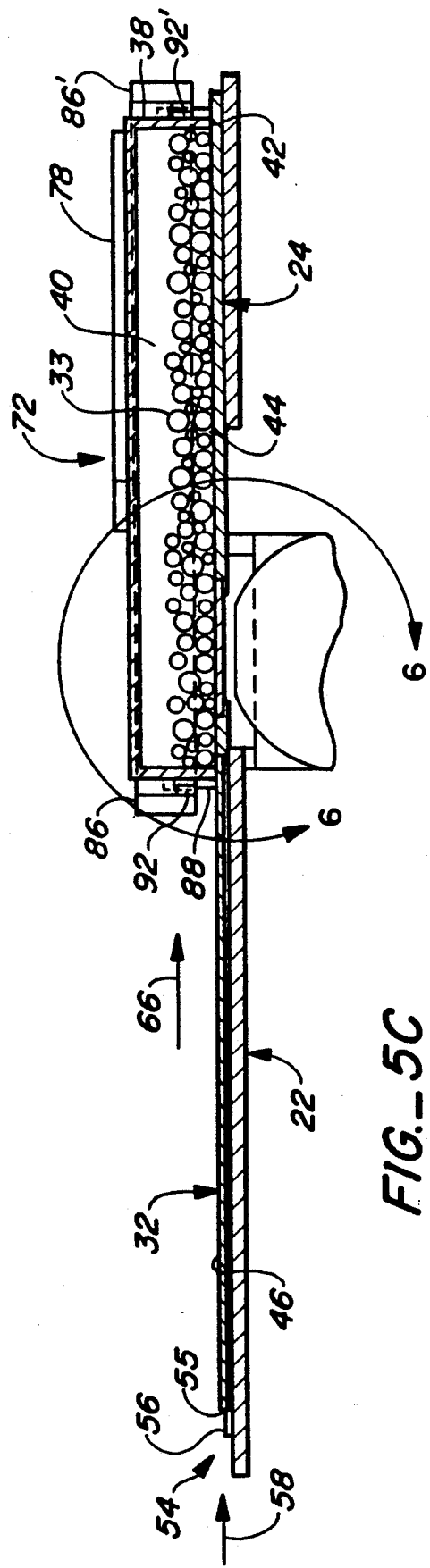

SAMPLE HOLDING AND POSITIONING MECHANISM AND METHOD FOR OPTICAL ANALYSIS

BACKGROUND OF THE INVENTION

1. Field of the Invention

The present invention relates, generally, to sample-holding mechanisms for analytical use and, more particularly, to sample-holding mechanisms and methods for use with optical analyzing instruments.

2. Description of the Related Art

Since the mid-sixties, optical analysis employing near-infrared (NIR) light energy has increasingly become the preferred method of determining the composition and constituent concentration of a sample, particularly grain. This technique is replacing the traditional, slightly more accurate, chromatographic or indirect separation chemical techniques which are generally substantially more time consuming. As compared to these traditional techniques, the current optical analyzing assemblies offer a diminishing precision gap, substantially shorter analyzing time intervals and a reduction of skilled personnel necessary for operation. Amongst other things, these factors account for the optical analyzing assemblies' commercial success. One particularly successful optical analyzer, for example, is the INFRAMATIC 8600 TM by Perten Instruments North America, Inc. which is a rapid, non-destructive, spectrophotometer designed for simultaneous multi-component analysis for most types of flour samples.

Briefly, it has been discovered that the chromophores composing a sample actively respond to at least one particular light energy wavelength, NIR, in general. More specifically, the absorptivity of the sample, as determined by quantitative diffuse reflectance or transmissivity of the preselected wavelength light incident on the sample, is a function of its composition and constituent concentration. Through correlation spectroscopy algorithms together with the appropriate spectroscopic measurements, the constituent concentrations, such as protein, moisture, starch and oil in grain, may be determined.

To analyze a grain specimen using light energy correlation spectroscopy, the sample is placed in a sample holder or cuvette and positioned in the optical pathway of light energy of a preselected wavelength. Typically, the range of preselected wavelength light energy corresponds to the NIR ranges which is emitted from a light source, such as wide band wavelength quartz tungsten-halogen light source. Subsequently, the absorptivity is measured by one of two types of NIR quantitative analysis instruments commercially available. One type measures the sample diffuse reflectance while the other measures the sample transmissivity. In either type, the reflectivity or transmissivity of the preselected wavelength light incident on the sample, as set forth above, is a function of its constituent concentration.

Optical analysis is particularly effective for quantitative compositional measurements on homogenous substances. For these substances, only a small particulate is necessary to compositionally represent the entire source. Such a small sample, because of its homogeneity, will not vary in composition from sample to sample. This is particularly useful when the concentration needs to be determined quickly, or when only a small quantity exists.

In contrast, when a sample is of a heterogenous composition, such as whole or ground grain, often a small sample is not truly representative of the entire composition. Therefore, a series of sub-measurements on a single sample or measurement of multiple sub-samples are necessary to cumulatively determine the composition and constituent concentrations. Depending on the accuracy required, the number of sub-measurements or of sub-samples is a function of the particle size of the sample and the variation in composition among the particles within the bulk.

Generally, the introduction of the sample or sub-sample into the optical pathway of the light source for irradiation is performed through manual positioning and repositioning. This involves the manual placement of the cuvette between the light source and a detection device to measure the diffuse reflectance or transmissivity. When a single sample is used for heterogenous compositions, the operator must manually reposition the sample, if multiple measurement are to be performed, to assure representation of the bulk. Regardless of the method (i.e., single sample or multiple sub-sample), such operator dependance, however, is often subject to a variety of procedural errors such as varying total procedure time which introduces drift errors; alignment errors which compound with multiple manual positioning operations; and potential operator indifference to complicated procedures. Moreover, reproducibility or duplication of the environmental conditions between each sub-sample, which adversely affects precision, is difficult to maintain. Such operational and procedural errors are fairly common.

Another positioning technique is to mechanically position the sub-samples or single sample in the optical pathway for irradiation. Some of these devices mechanically move the sample along the optical pathway to irradiate different areas of the sample specimen.

While these devices adequately and mechanically position or reposition the sample in a variety of locations with respect to the optical pathway, several inherent problems merit discussion. Generally, these apparatus are fairly complex units. Often these apparatus provide independent cuvettes or sample holding containers which are to be placed in complex tracking mechanism formed to move the cuvette past the analyzing window. To assure that the cuvette does not scratch or damage the analyzing window, the tracking mechanism must provide sufficient support to the cuvette so that contact is not made.

Typical of such an effort is the mechanical sample holder mechanism disclosed in U.S. Pat. No. 4,692,620 to Rosenthal. In this device, a cuvette filled with a specimen includes transparent viewing sides holding the specimen therein. The cuvette is coupled to a mechanical drive cam and positioned inside a tracking mechanism which facilitates movement of the cuvette across an analyzing window for irradiation by the optical analyzer. The cam further provides support to the cuvette so that there is no severe contact between the transparent surfaces of the cuvette and the analyzing window. In addition, the tracking mechanism fully encompasses the cuvette which discourages replacement or removal of the cuvette.

Moreover, preparation of individual samples or sub-samples for these apparatus, as well as for manually positioned sub-samples, is a tedious and labor intensive task. The operator must uniformly prepare and position the specimen into the cuvette to assure optimum optical quality and duplication between the sub-samples. Proper measurement procedure requires the specimen to be optically dense. Thus, not only must the specimen be firmly positioned in the cuvette, but, amongst other factors, this depends on the composition, optical characteristics of the composition and particle size.

Typically, a small quantity of the specimen is placed in a cuvette having two spaced apart, substantially parallel walls, at least one of which represents a transparent medium. Accordingly, if the sample holder is to be designed to hold a variety of specimens, to assure proper optical density, it is advantageous to provide a means for varying the depth of the specimen. This may be done by providing adjacent substantially parallel walls, as discussed above, which can be variable spaced. Rosenthal, for example, provides a movable cuvette capable of varying the specimen depth by providing movable transparent panels. Generally, these cuvettes are complex and require time consuming and labor intensive sample preparation.

More importantly, however, when multiple sub-samples are required or when multiple measurements are to sequentially performed at various location on a single sample, the optical characteristics and properties of each transparent medium location may need to be accounted for. This is especially true when precision is a primary consideration. In these instances, each transparent media location, even within the same sample, exhibits independent absorbent and reflective properties which increase the overall uncertainty in the measurements. Often three or four different sub-samples, or even three or four different locations on the same sub-sample, are required to attain the required accuracy, each of which feature independent optical characteristics. For precise constituent concentration determinations, these uncertainties are reduced by individually characterizing each media location, by determining a calibration or error factor, to compensate for its individual optical characteristics. Ultimately, such individual transmission properties may slightly vary the intensity of the incoming radiant light energy impinging the specimen. This may cause complications for low intensity irradiations of a sample, especially when multiple cuvettes are to be employed. Moreover, oily or wet samples often leave a residue on the cuvette windows which affects subsequent optical measurements.

This is particularly problematic with spectroscopic analyzing assemblies employing sample changer apparatus. Such a device is disclosed in U.S. Pat. No. 4,695,727 to Brierley. This device discloses a sample changer apparatus holding a plurality of sub-sample specimens which are automatically positioned in the optical pathway of the light source. As mentioned, when precision is desirable, each transmission location must be individually characterized which is not only labor intensive, but also highly prone to error when cuvette are removed and refilled, or broken and replaced.

Accordingly, it is an object of the present invention to provide a sample holder apparatus and method for use with an optical analyzing assembly which facilitates more precise and convenient spectroscopic analysis measurements.

It is another object of the present invention to provide a sample holder apparatus for use with an optical analyzing assembly which eliminates the need for preparing specimens of heterogeneous substances.

Still another object of the present invention is to provide a sample holder apparatus for use with an optical analyzing assembly which substantially reduces operational and procedural errors.

Yet another object of the present invention to provide a sample holder apparatus for use with an optical analyzing assembly which substantially reduces the need for individually characterizing each sample container or sample container position.

It is a further object of the present invention to provide an optical analyzing apparatus and method which is durable, compact, easy to maintain, has a minimum number of components, is easy to use by unskilled personnel, and is economical to manufacture.

The apparatus and method of the present invention has other objects and features of advantage which will be more readily apparent from the following description of the Best Mode of Carrying Out the Invention and the appended claims, when taken in conjunction with the accompanying drawing.

SUMMARY OF THE INVENTION

The present invention includes a sample holder apparatus and method for use with an optical analyzing assembly for irradiating a sample with light energy. Briefly, the sample holder apparatus of the present invention comprises a container mechanism with a wall defining a sample receiving volume and an opening defined by an edge portion of the wall. A partition mechanism is movably mounted to the wall and extends across the opening. The edge portion of the wall is suitably formed and dimensioned for slidable mating engagement with the partition mechanism. Furthermore, the sample holder apparatus includes a container support including a surface having an analyzing window portion transmitting light energy therethrough. The surface is suitably formed for slidable mating engagement with the edge portion of the wall. A transport mechanism is coupled to at least one of the container support and the container for producing relative movement therebetween to position the opening and the window in alignment for irradiation of the sample. The partition mechanism is mounted to the container for retraction from a closed position, across the opening, to an open position which exposes the sample during the relative movement. This is attained by sliding of the partition mechanism off the sample and by sliding of the sample onto the support surface and into alignment with the window portion for irradiation. The container edge portion slidably engages the container support surface during the relative movement to retain the sample in the container in substantially a same position during the relative movement.

These and other features and advantages of the present invention will become more apparent from the following description of exemplary embodiment thereof, as illustrated in the accompanying drawing.

BRIEF DESCRIPTION OF THE DRAWINGS

FIG. 1 is a top perspective view of the sample holder apparatus constructed in accordance with the present invention.

FIG. 2 is an enlarged top plan view of the sample holder apparatus shown in FIG. 1 without the housing.

FIG. 3 is an enlarged side elevational view, in cross-section, of the sample holder apparatus taken substantially along the plane of line 3—3 in FIG. 2.

FIG. 4 is an enlarged front elevational view, in cross-section, of the sample holder apparatus taken substantially along the plane of line 4—4 in FIG. 2 and illustrating the guidance mechanism.

FIGS. 5a–5c are a series of enlarged, partially of the sample holder apparatus taken substantially along the plane of line 5–5 in FIG. 2 and illustrating the sequential removal of the bottom wall as the container moves across the analyzing window.

FIG. 6 is an enlarged front elevational view, in cross-section, of the sample holder apparatus taken substantially along the bounded line 6—6 in FIG. 5c and more closely illustrating the transition between the partition and the container support.

FIG. 7 is an enlarged side elevation view, in cross-section, of the sample enclosure illustrating an alternative mounting mechanism between the container and the partition.

THE BEST MODE FOR CARRYING OUT THE INVENTION

The sample holder apparatus of the present invention employs a container device including a removable wall which is controllably removed so that a sample grain therein directly contacts an analyzing window for efficient irradiation of the sample. The following description is presented to enable a person skilled in the art to make and use the invention, and is provided in the context of a particular application and its requirements. Various modifications to the preferred embodiment will be readily apparent to those skilled in the art, and the generic principles defined herein may be applied to other embodiments and applications without departing from the spirit and scope of the invention. Thus, the present invention is not intended to be limited to the embodiment shown, but is to be accorded with the widest scope consistent with the principles and features disclosed herein.

As mentioned above, heterogenous samples often require four or more diffuse reflectance or transmissivity measurements for an effective representation of the bulk composition concentrations. The application becomes substantially complicated, as noted previously, when the independent optical characteristics of each transparent media location on a single cuvette or an multiple cuvettes (sub-samples) need to be factored into the constituent concentration calculations.

In accordance with the present invention, a sample holding apparatus is provided which permits the diffuse reflectance or transmissivity of a heterogeneous sample to be optically measured at a plurality of locations of the sample without requiring an individual optical characterization at each irradiation location. Attention is now directed to FIG. 1, where the subject sample holder apparatus, generally designated 20, is illustrated. Apparatus 20, briefly, comprises a platform 22 which includes a container support mechanism 24 having a upward facing surface 26. Fully integrated and flushly mounted with support surface 26 is a substantially transparent analyzing window member 28 capable of transmission of all light energy emitted from an optical analyzing apparatus (commonly known in the field and only partially represented in FIG. 3 as integration sphere 10). Positioned adjacent container support 24 is sample enclosure means, generally designated 29, which is dimensioned to securely retain a sample 33 therein. Enclosure means 29 may be provided by a box-like container 30, having a movable partition or wall 32. Container 30 is slidably positioned atop partition 32 which facilitates containment of sample 33. A transport mechanism, generally designated 36, incrementally and controllably moves container 30 off of partition 32, while still retaining sample 33 in substantially the same position inside container 30, and onto surface 26 of container support 24. This movement continues until sample 33 slidably contacts analyzing window member or pane 28 such that sample 33 intersects the optical pathway of analyzing apparatus 10. A housing 35 having a pivotal lid 37 helps prevent dust and external light from entering apparatus 20 during diffuse reflectance measurements.

The present invention eliminates the necessity for individually characterizing the specific transmission media especially when analyzing precision is sought. Primarily, sample holder apparatus 20 of the present invention permits the particles composing sample 33 to directly contact analyzing window 28 as container 30 moves relative to container support 24 and, hence, analyzing window 28. Accordingly, all measurements are recorded through the same location on analyzing window member 28. This eliminates the need for subsequent media optical adjustment aside from the single slope and bias calibration routinely performed to offset the optical characteristics of analyzing window member 28, which may vary among instrument systems.

Additionally, in accordance with the present invention, only a single sample needs to be prepared rather than multiple sub-samples. This reduces operator induced procedural errors, costs, and time for analysis. Furthermore, sample holder apparatus 20 provides an easy and efficient means for preparing a sample as gravity, not pressure from the apparatus, determines particle orientation and packing. Installation onto transport mechanism 36 is also simplified which will be described below.

As best viewed in FIG. 2, sample enclosure means 29 represents a cuvette or sample containing mechanism having circumferential wall members 38 which define a sample holding cavity 40 therein. Lower edge portions 42 of wall members 38, as shown in FIGS. 3 and 6, define a downwardly facing opening 44 to cavity 40. As will be described in greater detail below, downwardly facing opening 44 provides optical access to cavity 40 where sample 33 is contained for irradiation by optical analyzing apparatus 10 as opening 44 is controllably positioned in the optical pathway.

Preferably, sample enclosure means 29 is a substantially rectangular shaped member where wall members 38 are upstanding and substantially planar. As will be apparent from the description henceforth, however, the shape and dimension of wall members 38, with a few exceptions, may vary considerably. It will be appreciated that wall members 38 must be shaped to retain sample 33 therein in substantially the same position with respect to sample enclosure 29 as the walls are controllably moved onto container support 24, as will be discussed below.

As mentioned above, container 30 is positioned in a generally upside down orientation atop partition mechanism 32. Partition 32 is formed to substantially cover opening 44 so that sample 33 may be retained in container 30. However, in order to irradiate sample 33 with light energy and to position sample 33 in direct contact with analyzing window 28, partition 32 must be moved with respect to container 30 so that opening 44 may directly positioned in the optical pathway of analyzing apparatus 10. Relatively speaking, partition 32 is retracted from a closed position, covering opening 44, to an open position. As best viewed in FIGS. 5a-5c, transport mechanism 36, described in greater detail below, movably reposition container 30 from atop partition 32 onto surface 26 of container support 24 to a position atop window member 28. In the preferred embodiment, container 30 is the component which is moved relative to a stationary container support 24; however, it will be appreciated that in an alternative embodiment of the present invention, the container support 24 may move relative to a stationary container 30.

As container 30 is controllably moved from atop partition 32 to surface 26 of container support 24, downwardly facing edge portions 42 of wall members 38 slidably engage both an upwardly facing surface 46 of partition mechanism 32 and support surface 26, simultaneously. FIG. 5b illustrates that the transition from partition surface 46 to support surface 26 is substantially aligned so as not to disturb the relative positioning of particulate material of sample 33. Accordingly, in order to maintain sample 33 in a relatively similar position during movement, edge portion 42 must be suitably formed and dimensioned to slidably contact and matingly engage both partition surface 46 and support surface 26. Such engagement, together with the consolidation of the particles composing sample 33 (discussed below), causes the particulate to be dragged over partition surface 46 to support surface 26 without substantial tumbling of the particulate material. In addition, both partition surface 46 and support surface 26 are provided with substantially smooth surfaces, which aids in the maintenance of the same relative position of the particles of sample 33, as well as permitting edge portion 42 to slide easily.

Turning now to FIG. 6, it can be seen that partition surface 46, support surface 26 and wall edge portion 42 are all substantially aligned in a common plane during the transition of container 30 and sample 33 onto container support 24. Such a planar relationship provides continuous slidable and matingly engageable contact between edge portions 42, and partition surface 46 and support surface 26. Moreover, these planar surfaces are relatively easy to maintain as well as to manufacture. It will be appreciated, however, that both partition 32 and support surface 26 could conceivably be curved or otherwise complementary shaped as long as they both matingly engage edge portions 42 so that sample 33 is stably positioned therein during movement.

Partition 32 seats against a plurality of posts 48, shown in FIG. 6, which permits partition surface 46 to be aligned in the same plane as support surface 26. Thus, posts 48, while providing support to partition 32 and container 30, can easily be adjusted so that partition surface 46 is properly aligned with support surface 26.

As has been discussed, in the preferred embodiment, both partition 32 and container support 24 are to remain substantially stationary during the relative movement of container 30 onto support surface 26. It will be noted, however, that container 30 could be stationary while both partition 32 and container support 24 move relative to container 30. Regardless, as best viewed in FIG. 2 and as will be described in greater detail below, partition 32 is disposed substantially adjacent container support 24 when container 30 is initially mounted to sample holder apparatus 20. During relative movement of container 30 with respect to container support 24, a side edge 50 of partition 32 matingly abuts a shoulder or barrier 52 which does not permit partition 32 to advance beyond it. Thus, partition 32 remains in substantially the same position throughout the measuring sequence.

In the preferred embodiment, barrier 52 is essentially the side edge of container support 24 which oppositely opposes partition edge 50. Accordingly, as transport mechanism 36 urges container 30 onto support surface 26, partition 32 is stationarily retained as partition edge 50 abuts barrier 52, permitting container edge portion 42 to slidably and matingly engage partition surface 46 and support surface 26. Subsequently, sample 33 is drawn over and in contact with analyzing window 28 so that the diffuse reflectance of sample 33 may be measured. Incidently, although the present invention is primarily and preferably described for use in diffuse reflectance optical analyzing apparatus, such as integrating spheres, sample holder apparatus 20 may be easily modified to measure the transmissivity through sample 33.

In an alternative embodiment, partition 32 may be urged against barrier 52 by a positioning mechanism 54 which includes an upstanding post 56 dimensioned to engage an opposing partition edge 55, as show in FIGS. 5a-5c. During placement of sample enclosure means 29 onto platform 22 of apparatus 20 (discussed below), positioning mechanism 54 slidably positions post 56, in the direction of arrow 58, against opposing partition edge 50 and urges sample enclosure 29 against barrier 52 so that partition 32 is removably retained. The slidable positioning of post 56 may be operated by most electro-mechanical actuator devices, such as a solenoid (not shown).

Referring now to FIG. 6, container support member 24 is formed with a strategically positioned aperture 60 extending therethrough. Optical analyzing apparatus 10 is aligned with aperture 60 so that the optical pathway may be directed through aperture 60. Analyzing window member 28 is flushly positioned in aperture 60 so that the upward facing surface of window pane 28 is substantially aligned in the same plane containing support surface 26 and partition surface 46. This positioning further assures that container edge portion 42 slides smoothly thereover and that sample 33 remains relatively undisturbed as it passes over window 28. As shown in FIG. 6, a ledge portion 62, formed in container support 24 and extending radially into aperture 60, provides support for analyzing window member 28 to seat against.

Preferably window 28 is composed of quartz or the like which minimizes transmissive distortion as the light energy passes therethrough. Moreover, quartz window 28 is formed to provide a sufficiently smooth surface for wall edge portion 42 to slide over. Virtually any transparent member or pane, however, may be used.

Briefly, it will be noted that partition 32 is initially movably mounted to container wall edge portions 42 through magnetic means 64 sufficient to releasably retain partition 32 thereagainst for most operational purposes. This is particularly useful when sample enclosure means 29 is turned upside down for positioning on platform 22. Thus, the magnetic attraction must be sufficient to not only retain partition 32 in a stable condition against wall edge portions 42, but also to sustain the additional weight of sample 33 as it seats against partition surface 46. However, although the magnetic attraction is substantial between the opposing surfaces, it is not sufficient to prevent the slidable movement of container 30 onto container support 24, as set forth above. Similarly, it is preferable that container wall edge portions 42 be magnetically attracted to surface 26 of container support 24 so that container edge 42 maintains a tight seal to surface 26 throughout its travel. This, of course, prevents spillage of sample 33.

In the preferred form, as shown in FIG. 2, magnetic strips 64 are embedded in or positioned flush with wall edge portions 42 so as not to impede the slidability and mating engagement between wall edge portions 42 and partition surface 46. It is, of course, imperative that partition 32 be composed of or include a magnetically attractive material disposed around at least the periphery of partition surface 46 so that partition 32 will be attracted thereto. Preferably, partition 32 is composed of a ferromagnetic material, as is surface 26 of container support 24. Alternatively, the magnetic attraction may be created electro-magnetically or partition 32 itself may include the magnetic strips without departing from the true spirit and nature of the present invention.

Accordingly, upon the initial preparation of heterogenous sample 33, container 30 is oriented (while not mounted to sample holder apparatus 20) so that opening 44 faces upward. A quantity of sample 33 is placed into container cavity 40. Subsequently, partition 32 is alignably positioned over container opening 44 where wall edge portions 42 contact partition surface 46. Magnetic strips 64 releasably retain partition 32 to wall edge portions 42 so that enclosure 29 may be turned over and oriented face down on holder apparatus 20.

Alternatively, as represented in FIG. 7, partition 32 may be slidably coupled to container 30 through a mating partition mounting assembly 67. The exterior surfaces of front and rear walls 38a and 38b may be formed with guidance grooves 69 extending substantially longitudinally proximate edge portions 42. Partition 32 includes complementary guidance ribs 71 extending from the side walls of partition 32 in the direction of container opening 44, as shown in FIG. 7. Guidance ribs 71 are formed to slidably insert into grooves 67 for mating engagement therebetween. It will be understood that partition mounting assembly 67 also could be provided by ribs on walls 38 and mating grooves on cover or partition 32. Thus, in this embodiment, partition 32 does not need to be magnetically attracted to wall edge portions 42 because mating mounting assemblies 67 provide the necessary movable partition mounting structure.

Moreover, it will be appreciated that container support 24 may have complementary guidance ribs (not shown) and have a cross-section area substantially similar to partition 32 (of FIG. 7). Thus, when properly aligned, container 30 slidably moves off partition 32 where guidance grooves 69 matingly receive the guidance ribs (not shown) of container support 24 so that sample 33 may come in direct contact with analyzing window 28. Attention is now directed to FIGS. 2 and 3 where transport mechanism 36 will be discussed in detail. Transport mechanism 36 preferably positions opening 44 of container 30 over analyzing window 28 so that analyzing apparatus 10 irradiates sample 33. In the preferred form, transport mechanism, generally designated 36, moves container 30 horizontally in the direction of arrow 66 (FIGS. 5a–5c) which is substantially linear. Accordingly, mechanism 36 can maneuver opening 44, and hence sample 33, to any linear position along analyzing window 28. It will be appreciated that transport mechanism 36 may be easily constructed so as have two degrees of freedom. In some instances, two-dimensional movement of container 30 may be necessary.

As best viewed in FIG. 2, transport mechanism 36 includes a conventional electro-mechanical motor 68, a carriage 72 and an arm 74 mounted to carriage 72 and engaging container 30. Motor 68 is drivably coupled, via belt 76, to a threaded drive shaft 80. Carriage 72 generally comprises a plate member 78 rigidly coupled to a drive bearing 79 which is dimensioned to matingly threadably engage threaded shaft 80. Accordingly, as motor 68 rotates in a clockwise or counter-clockwise direction, belt 76 drives threaded shaft 80 which urges drive bearing 79, and hence plate member 78, along drive shaft 80. Carriage 72 preferably includes at least two guide bearings 82 and 82' which facilitates guidance of plate member 78 along a smooth guide shaft 84. Preferably, drive shaft 80 and guide shaft 84 are positioned substantially parallel each other and shaft 80 is rotatably anchored at opposing distal ends.

Engaging arm 74, as shown in FIG. 3, is rigidly coupled to plate member 78 so that arm 74 moves in concert with carriage plate member 78. Extending perpendicularly outward from arm 74, in a direction away from plate 78, are rigid cantilever members 86 and 86'. Cantilever members 86 and 86' are positioned parallel one another and straddle the opposing container wall end members 38. The distal ends of cantilever members 86 and 86' include finger portions 92 and 92' projecting outward toward respective mounting members 88 and 88' which are rigidly affixed to the sides of opposing end wall members 38. As best illustrated in FIGS. 3 and 6, mounting members 88 and 88' are formed with recesses 90 and 90' which are dimensioned to receive respective fingers portions 92 and 92'. Recesses 90 and 90' include a channel extending to wall edge portions 42 which permit finger portions 92 and 92' to slide up into recesses 90 and 90' as the sample enclosure means is lowered onto fingers 92 and 92'. Upon mating engagement, sample enclosure means 29 will be removably mounted to sample holder apparatus 20 through transport mechanism 36. Thus, motor 68 may movably urge container 30 and sample 33 to any position along the direction of arrow 66.

In the preferred form, motor 68 is a conventional electro-mechanical type. In an alternative embodiment, however, the present invention may include a stepping motor 68 if desirable. Moreover, the present invention preferably includes an electronic controller 96 which automatically controls synchronization of container 30 with respect to optical analyzer. The electronic controller 96 may control the motor speed, container positioning and positioning mechanism 54. Hence, a positioning sensor 94 may be necessary which tracks the movement and location of container 30 with respect to analyzing window 28. Sensor 94 may comprise any common mechanical, electro-mechanical or optical sensing device.

Accordingly, the operation of the apparatus and the method of the present invention can be described. After sample 33 has been prepared and placed in cavity 40, as set forth above, sample enclosure means 29 is ready for mounting to holder apparatus 20. As mentioned, the preferred orientation of sample enclosure 29 is in an upside down position where container opening 44 faces analyzing window 28. Upon mounting to transport mechanism 36, sample enclosure 29 is positioned above cantilever members 86 and 86' and aligned so that recesses 90 and 90' are directly over corresponding finger portions 92 and 92'. The channel to recess 90 and 90' preferably is tapered to allow convenient placement and to give precise final positioning relative to mechanism 36. As best viewed in FIG. 3, sample enclosure 29 is subsequently lowered downward onto cantilever members 86 and 86' where finger portions 92 and 92' are slidably positioned in recesses 90 and 90'. In this orientation, the particulates of sample 33 gravitationally consolidate and compact against upper partition surface 46, and sample 33 substantially uniformly and evenly distributes in the container over opening 44. This provides the appropriate optical density necessary for that specific specimen. Once partition 32 is firmly seated against posts 48, enclosure means 29 is operably mounted to sample holder apparatus 20.

Subsequently, partition positioning means 54 engages opposing partition edges 50, thereby firmly gripping partition 32 between stop 56 and barrier shoulder 52. Transport mechanism 36 engages container 30 and slidably moves container 30 and sample 33 onto support surface 26 in a controlled manner. During this transition, wall members 38 provide sufficient lateral support for sample 3 to retain it in substantially the same position as it moves onto and across support surface 26. As shown in the sequential series illustrated in FIGS. 5a-5c, as partition 32 is retained, the particles composing sample 33 substantially retain their relative positioning as they are positioned in direct contact with analyzing window 28. Accordingly, diffuse reflectance measurements may be conducted at a plurality of locations along container opening 44 so that sample 33 is properly represented. These measurements may be performed while container 30 is moving or when it is stationary. After the appropriate number of measurements have been conducted, transport mechanism 36 may reverse its direction and slidably urge container 30, and hence sample 33, back over partition 32 where magnetic coupling between magnetic strips 64 and partition surface 46 is again made. Sample enclosure 29 can then be removed from holder apparatus 20.

In the preferred form, as mentioned above and as shown in FIG. 1, apparatus 20 includes a housing 35 having a pivotal lid 37. Housing 35 ensures optimum optical measurements during operation by substantially preventing dust and undesirable light rays from entering apparatus 20. Pivotal lid 37 provides access to engaging arm 74 and cantilever members 86 and 86' so that container means 29 can be mounted in the transport assembly.

While the invention has been described in connection with what is presently considered to be the most practical and preferred embodiments, it is to be understood that the invention is not limited to the disclosed embodiment but, on the contrary, is intended to cover various modifications and equivalent arrangements included within the spirit and scope of the appended claims.

Therefore, persons of ordinary skill in this field are to understand that all such equivalent structures are to be included within the scope of the following claims.

What is claimed is:

1. A sample holder apparatus for use with an optical analyzing assembly for irradiating a sample with light energy, said holder apparatus comprising:

container means with a wall defining a sample receiving volume and an opening defined by an edge portion of said wall;

partition means movably mounted to said wall and extending across said opening, said partition means being formed and dimensioned for slidable mating engagement with said edge portion of said wall;

a container support including a surface having an analyzing window portion transmitting light energy therethrough, said edge portion of said wall being formed for slidable mating engagement with said surface of said container support;

transport means coupled to at least one of said container support and said container and producing relative movement therebetween to position said opening and said window in alignment for irradiation of said sample; and said partition means being mounted to said container for retraction from a closed position, across said opening, to an open position, exposing said sample during said relative movement, by sliding of said partition means off said sample and by sliding of said sample onto said support surface and into alignment with said window portion for irradiation, and said container edge portion slidably engaging said support surface during said relative movement to retain said sample in said container in substantially a same position during said relative movement.

2. The sample holder apparatus as defined in claim 1 wherein,
    said partition means is substantially planar.

3. The sample holder apparatus as defined in claim 1 wherein,
    said transport means includes drive means and carriage means movably coupled to said drive means and to at least one of said container support and said container for producing relative movement therebetween.

4. The sample holder apparatus as defined in claim 3 wherein,
    said carriage means is positioned to removably receive said container means.

5. The sample holder apparatus as defined in claim 3 wherein,
    said drive means comprises a motor and a drive screw rotatably coupled to said motor, said carriage means being movably mounted to said drive screw.

6. The sample holder apparatus as defined in claim 3 wherein,
    said transport means further includes guide means upon which said carriage means is slidably mounted for guiding during said relative movement along a predetermined path.

7. The sample holder apparatus as defined in claim 6 wherein,
    said predetermined path is linear.

8. The sample holder apparatus as defined in claim 3 wherein,
    said carriage means includes a rigid arm assembly dimensioned to slidably receive said container means therein.

9. The sample holder apparatus as defined in claim 3 further including:
    sensor means coupled to said transport means for sensing the position of said container means with respect to said container support.

10. The sample holder apparatus as defined in claim 3 further including:
    controller means coupled to said transport means for controlling said relative movement in synchronization with the operation of said optical analyzing assembly.

11. The sample holder apparatus as defined in claim 1 wherein,
said relative movement is linear.

12. The sample holder apparatus as defined in claim 1 wherein,
said container means is rectangular shaped.

13. The sample holder apparatus as defined in claim 1 wherein,
said container support is mounted to an adjacently disposed platform member.

14. The sample holder apparatus as defined in claim 13 wherein,
said transport means is mounted to said platform member.

15. The sample holder apparatus as defined in claim 1 further including:
stop means positioned adjacent said partition means for retaining said partition means in a stationary position relative said container means during said relative movement to said open position.

16. The sample holder apparatus as defined in claim 15 wherein,
said, stop means comprises a barrier shoulder dimensioned to abut against a side portion of said partition means retaining said partition means in said stationary position.

17. The sample holder apparatus as defined in claim 16 wherein,
said partition is aligned adjacent said container support such that during said relative movement, said edge portion of said container means slides from said partition onto said support surface.

18. The sample holder apparatus as defined in claim 1 further including:
mounting means movably mounting said partition means to said wall for slidable mating engagement therebetween.

19. The sample holder apparatus as defined in claim 18 wherein,
said mounting means is provided by magnetic means.

20. The sample holder apparatus as defined in claim 18 wherein,
said mounting means is provided by a mating groove and rib assembly.

21. The sample holder apparatus as defined in claim 20 wherein,
said groove rib assembly comprises at least one longitudinal guidance groove extending along said wall proximate said edge portion, and at least one complementary guidance rib coupled to said partition means and positioned for slidable mating engagement with said guidance groove.

22. A method of positioning a sample for irradiation with energy by analyzing apparatus comprising the steps of:
placing said sample in a container having a movable partition;
mounting the container to a transport assembly proximate a container support surface having an irradiation window therein; and
sliding said partition from said container by moving at least one of said container and said container support surface while sliding said sample while in said container onto said container support surface until said sample is positioned in alignment with said irradiation window for irradiation.

* * * * *

UNITED STATES PATENT AND TRADEMARK OFFICE
CERTIFICATE OF CORRECTION

PATENT NO. : 5,227,856
DATED : July 13, 1993
INVENTOR(S) : David S. Reed, et. al.

It is certified that error appears in the above-indentified patent and that said Letters Patent is hereby corrected as shown below:

Column 11, line 22, delete "3" and insert --33--.

Signed and Sealed this

Fifteenth Day of March, 1994

Attest:

BRUCE LEHMAN

Attesting Officer

Commissioner of Patents and Trademarks